US009747413B2

(12) United States Patent
Zidan et al.

(10) Patent No.: US 9,747,413 B2
(45) Date of Patent: Aug. 29, 2017

(54) ADAPTIVE PROCESSING FOR SEQUENCE ALIGNMENT

(75) Inventors: M. Affan Zidan, Thuwal (SA); Talal Bonny, Thuwal (SA); Khaled N. Salama, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 1178 days.

(21) Appl. No.: 13/185,849

(22) Filed: Jul. 19, 2011

(65) Prior Publication Data

US 2012/0023110 A1 Jan. 26, 2012

Related U.S. Application Data

(60) Provisional application No. 61/366,065, filed on Jul. 20, 2010.

(51) Int. Cl.
*G06F 19/00* (2011.01)
*G06F 19/22* (2011.01)
*G06F 19/28* (2011.01)

(52) U.S. Cl.
CPC .............. *G06F 19/22* (2013.01); *G06F 19/28* (2013.01)

(58) Field of Classification Search
None
See application file for complete search history.

(56) References Cited

PUBLICATIONS

International Search Report and Written Opinion in Application No. PCT/IB2011/003020 dated Oct. 15, 2012, 13 pages.

Manavski et al., "CUDA compatible GPU cards as efficient hardware accelerators for Smith-Waterman sequence alignment", BMC Bioinformatics, BioMed Central, London (GB), vol. 9, No. Suppl 2, Mar. 26, 2008, 9 pages.

Ligowski et al., "An Efficient Implementation of Smith Waterman Algorithm on GPU Using CUDA, for Massively Parallel Scanning of Sequence Databases", Interdisciplinary Centre for Mathematical and Computational Modelling, University of Warsaw, Warsaw (Poland), Parallel & Distributed Processing, May 23, 2009, 8 pages.

Farrar, "Striped Smith-Waterman speeds database searches six times over other SIMD implementations", Bioinformatics, published by Oxford University Press, vol. 23, No. 2, Jan. 15, 2007, 6 pages.

Bonny et al., "An Adaptive Hybrid Multiprocessor Technique for Bioinformatics Sequence Alignment", 5th Cairo International Biomedical Engineering Conference, Cairo (Egypt), Dec. 16-18, 2010, 4 pages.

*Primary Examiner* — Anna Skibinsky
(74) *Attorney, Agent, or Firm* — Thomas | Horstemeyer, LLP

(57) ABSTRACT

Disclosed are various embodiments for adaptive processing for sequence alignment. In one embodiment, among others, a method includes obtaining a query sequence and a plurality of database sequences. A first portion of the plurality of database sequences is distributed to a central processing unit (CPU) and a second portion of the plurality of database sequences is distributed to a graphical processing unit (GPU) based upon a predetermined splitting ratio associated with the plurality of database sequences, where the database sequences of the first portion are shorter than the database sequences of the second portion. A first alignment score for the query sequence is determined with the CPU based upon the first portion of the plurality of database sequences and a second alignment score for the query sequence is determined with the GPU based upon the second portion of the plurality of database sequences.

16 Claims, 11 Drawing Sheets

| Query | GPU + CPU | GPU + 2CPUs | GPU + 3CPUs |
|---|---|---|---|
| P0C0D4 (114) | 65.00 | 49.73 | 40.38 |
| P01111 (189) | 63.00 | 44.33 | 37.26 |
| P00762 (246) | 57.40 | 41.53 | 32.80 |
| P57305 (286) | 56.20 | 41.41 | 33.33 |
| P20505 (300) | 55.00 | 41.50 | 31.20 |
| P10318 (362) | 52.35 | 36.93 | 29.00 |
| P07327 (374) | 52.60 | 37.53 | 30.12 |
| P12031 (410) | 52.20 | 38.76 | 29.85 |
| P10635 (497) | 51.10 | 35.33 | 29.00 |
| P08800 (511) | 51.00 | 36.43 | 29.20 |

Percentage of sequence database assigned to GPU

FIG. 9

ADAPTIVE PROCESSING FOR SEQUENCE ALIGNMENT

CROSS REFERENCE TO RELATED APPLICATIONS

This application claims priority to U.S. provisional application entitled "APPARATUS, SYSTEM, AND METHOD FOR A HYBRID GPU/CPU TECHNIQUE FOR HIGH-SPEED PROCESSING" having Ser. No. 61/366,065, filed Jul. 20, 2010, which is entirely incorporated herein by reference.

BACKGROUND

Sequencing applications process large databases of sequences to identify relationships between sequences. DNA and protein data base sequence alignment are among the most important applications in bioinformatics. Increasing interest in studying the structure and the function of DNA, RNA and proteins, and correlating this information with diseases is driving exponential growth in the bioinformatics market. Such information helps researchers to identify drug leads and other therapeutic modalities. However, as the amount of sequence data being examined increases, the computation time of the sequencing applications grows at a staggering rate.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIGS. 9 and 10 are graphs illustrating the improvement in performance using the hybrid GPU/CPU evaluation of FIG. 5 in accordance with various embodiments of the present disclosure.

DETAILED DESCRIPTION

Figure 1:
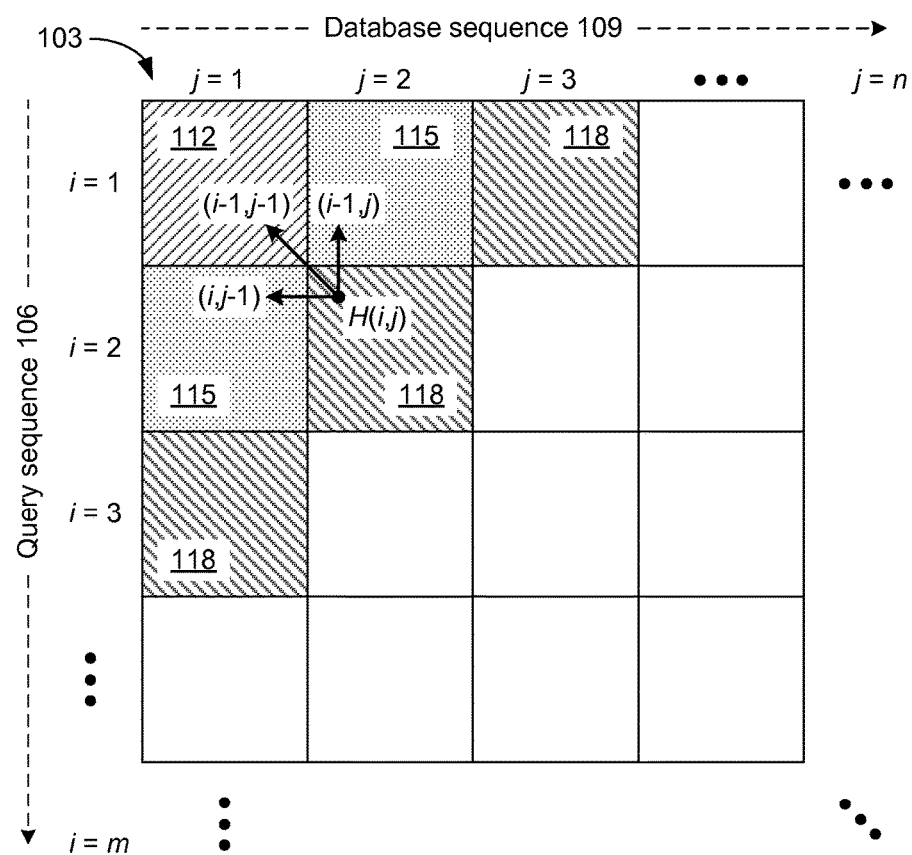
FIG. 1 is a graphical representation of a similarity matrix for determination of sequence alignments in accordance with various embodiments of the present disclosure.

Disclosed herein are various embodiments of methods and systems related to adaptive processing for sequence alignment. Reference will now be made in detail to the description of the embodiments as illustrated in the drawings, wherein like reference numbers indicate like parts throughout the several views.

Sequence database applications, such as sequence comparing, sequence searching and sequence matching, etc., are used in a variety of research areas for different purposes such as video, audio, or image copy detection, text plagiarism detection, DNA or protein sequence matching, etc. These applications often consume large amounts of computation time because they are based upon searching for matches or near matches by comparing a given pattern (or sequence) with large numbers of patterns (or sequences) stored in a database. These searches process large amounts of data. For instance, a database such as, e.g., a protein database may exceed 11 GB in size. As a result, these applications may take hours of processing time to obtain a solution.

Using a hybrid graphical processing unit (GPU)/central processing unit (CPU) system to implement the sequence alignment applications can improve processing performance and time to solution. GPUs are increasingly being deployed for applications reserved for CPUs. Hybrid GPU/CPU systems include both a GPU and one or more CPU(s) for processing. For example, a processor may include a GPU and multi-core CPUs on one chip. A GPU may be included with a plurality of CPUs in a single package. Utilizing both the GPU and CPU(s) to simultaneously implement the application computations can improve the performance of sequence alignment applications. Appropriate distribution of the application processing between the GPU and CPU(s) may result in improvements by a factor of two or more.

Usually, a sequence database contains a variety of sequences having different sequence lengths. The sequences may be processed on either a CPU or a GPU. However, running the short sequences of the database on a GPU is not as efficient as running the long sequences on the GPU. By processing the long sequences of the sequence database on the GPU and simultaneously processing the short sequences on the CPU(s), the speed of the sequence alignment application may be efficiently increased. By appropriately distributing the data-base sequences between the GPU and CPU(s), the GPU cores are efficiently engaged throughout the entire computing cycle.

A sequence alignment application may implement any of a variety of sequence alignment algorithms such as, but not limited to, the Smith-Waterman (SW) algorithm, the Gotoh algorithm, or the Alschul and Erickson algorithm. The SW algorithm is based on the idea of comparing segments of all possible lengths between two sequences to identify the best local alignment and it guarantees that it will identify the optimal alignment of two sequences. The first sequence is called the query sequence and the second sequence is called the database sequence. The SW algorithm can take a long time to compute because its computing and memory requirements grow quadratically with the size of the sequence database.

The SW algorithm may be used for sequence alignment procedures in, e.g., bioinformatics. It is a dynamic programming method that may be used for identifying similarities between nucleotide or protein sequences. The SW algorithm begins by computing a similarity matrix score associated with the two sequences. Referring to FIG. 1, shown is a graphical representation of an example of a similarity matrix 103. The similarity matrix 103 has two dimensions 106 and 109, the first for the query sequence and the second for the database sequence, respectively. If the query sequence includes m elements and the database sequence has n elements, then the similarity matrix 103 is an m×n matrix. The SW algorithm assigns an alignment score, H(i,j), to each cell based upon a comparison between the two sequences. The highest scoring position in the matrix represents the optimal alignment of the two sequences (i.e., the query and database sequences). The equations for computing the alignment score, H(i,j), are as follows:

$$E(i, j) = \max \begin{cases} E(i, j-1) - G_{ext} \\ H(i, j-1) - G_{open} \end{cases} \quad \text{EQN. 1}$$

$$F(i, j) = \max \begin{cases} F(i-1, j) - G_{ext} \\ H(i-1, j) - G_{open} \end{cases} \quad \text{EQN. 2}$$

$$H(i, j) = \max \begin{cases} 0 \\ E(i, j) \\ F(i, j) \\ H(i-1, j-1) - W(q_i, d_j) \end{cases} \quad \text{EQN. 3}$$

such that E(i,j) and F(i,j) are the maxima of the following two items: open a new gap and keep extending an existing gap. The $W(q_i,d_j)$ is the score substitution matrix, which differs depending on the type of sequence.

As illustrated in FIG. 1, the alignment score, H(i,j), of any cell in the similarity matrix 103 depends on the scores of three adjacent cells: the left cell, H(i,j−1), the up cell, H(i−1,j), and the up-left cell, H(i−1,j−1). This means that the scores of cells located on the anti-diagonal positions (i,j−1) and (i−1,j) are computed before computing the score of cell (i,j). Computing the score of a cell may be considered a sub-problem and the optimum score for the similarity matrix 103 may be considered as the general problem. Each sub-problem may be run on a different thread in parallel with another sub-problem running on another thread if there is no data dependency between them.

Figure 2:
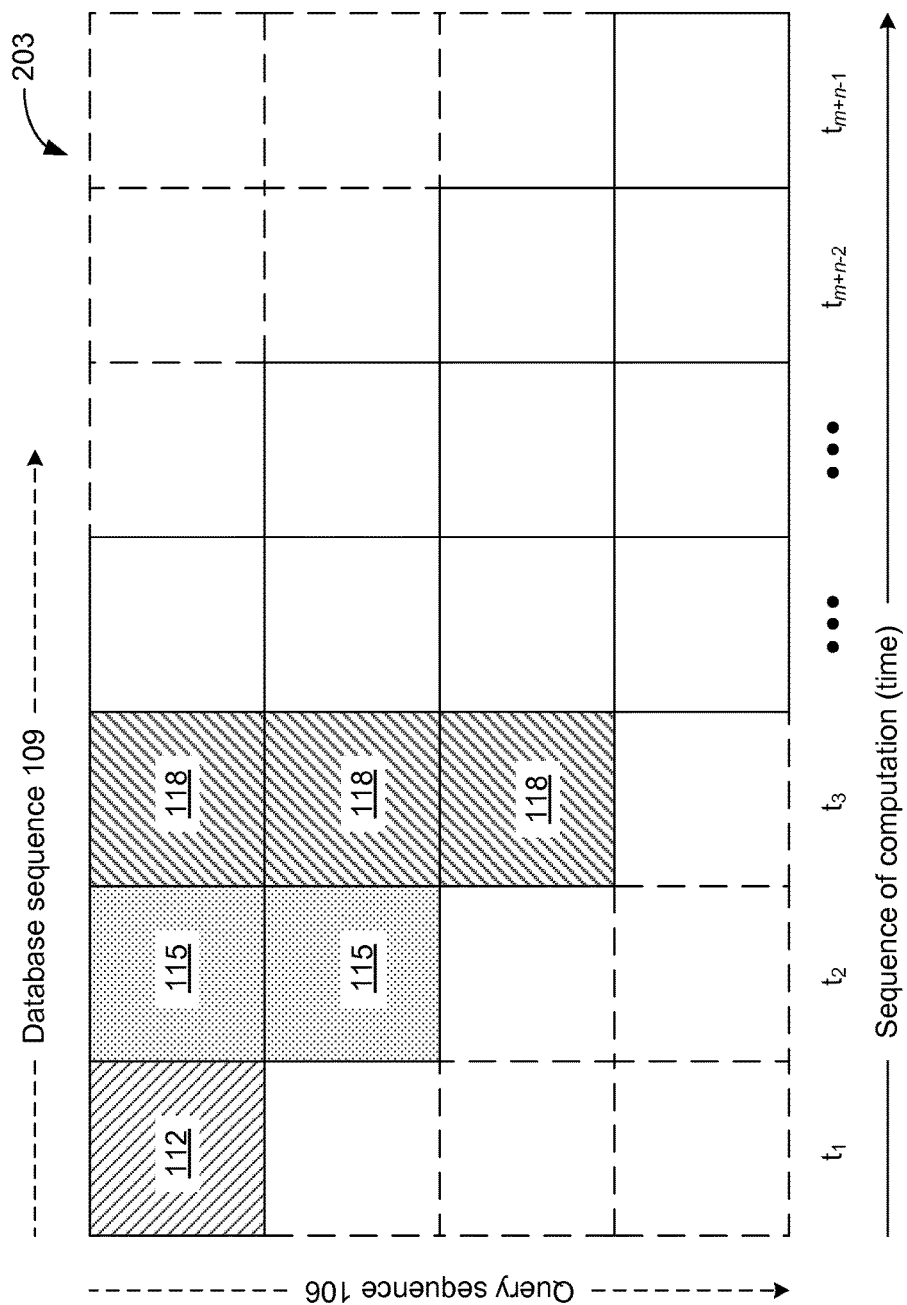
FIG. 2 is a graphical representation of a computational sequence of the similarity matrix of FIG. 1 in accordance with various embodiments of the present disclosure.

Referring next to FIG. 2, shown is a graphical representation of an example of the computational sequence 203 of the similarity matrix 103 of FIG. 1. Cells 115 can be computed independently each other after cell 112 has been computed. Similarly, cells 118 can be computed independently of each other after cells 115 have been computed. Thus, all the cells located on the same anti-diagonal positions may be computed simultaneously on different threads. When the similarity matrix 103 is computed using a GPU, not all the GPU cores will be used to compute the similarity matrix 103 during the whole computational sequence 203. In particular, at the beginning and at the end of the computational sequence 203, some GPU cores will not be involved in the computation because of the limited number of threads that can be computed simultaneously.

In the example of FIG. 2, at moment $t_1$, only one GPU core is involved in computing the alignment score of one cell 112 and m−1 cores are idle. At moment $t_2$, two GPU cores are busy computing the alignment scores of two cells 115 and m−2 cores are idle. The number of GPU cores continues to increase for each computational moment. If the database sequence 109 is the same length or longer than the query sequence 106 (n≥m), then a total of m cores will be engaged computing alignment scores during a portion of the computational sequence 203. The opposite scenario happens at the end of the computational sequence 203 with a decreasing number of GPU cores computing alignment scores until only one GPU core is involved in computing the alignment score of the last cell. Clearly, when the database sequence 109 is long, the time the GPU cores are idle may be ignored in comparison with the computational time of the GPU cores. But, when the database sequence 109 is short, the idle time has a larger negative effect on the performance of the matrix computation and may not be ignored.

The negative effect is also present when evaluating the alignment of a query sequence with a database sequence including sequences with different lengths. Databases including sequences of a variety of lengths are used in areas such as, e.g., bioinformatics. For example, the SWISS-PROT protein database includes large number of sequences with different lengths (starting from 2 residues to almost 12000 residues). Because the SWISS-PROT database has many short length sequences in comparison to the length of a query, computing the similarity matrix for the sequence using only GPU cores may result in poor performance. Using a hybrid GPU/CPU technique, a similarity matrix for the longer sequences of the database may be computed by the GPU cores, while the CPU may be used to compute a similarity matrix for shorter sequences. Both the GPU cores and the CPU may run simultaneously and finish their collective tasks in less time than it would take for each to individually complete the computations.

In some embodiments, the database sequences are sorted according to their length from the longest to the shortest sequences. After sorting the database, the database sequences may be distributed between a GPU and a CPU, such that the long sequences are sent to the GPU and the short ones are sent to the CPU. A query sequence is obtained and used by both the GPU and the CPU to compute a similarity matrix for each group of database sequences. The GPU and the CPU each determine the highest alignment score for the query sequence. The highest alignment score found by the GPU may then be compared with the highest alignment score found by the CPU to determine the maximum score and thus the final result for aligning the query sequence with the database sequences.

The distribution of the database sequences between the GPU and CPU directly affects the performance of the matrix computations. The number of short sequences assigned to the CPU and the number of the long sequences assigned to the GPU may be based on the time required for each processor to finish its task. In some embodiments, when the database sequences are distributed between the GPU and the CPU, such that they run simultaneously and finish their tasks at the same time or substantially the same time, the highest performance may be achieved.

To measure the performance of a sequence alignment in computational biology, the Cell Updates per Second (CUPS) metric is commonly used. The total number of cell updates reveals the execution performance of a sequence alignment algorithm. The method to compute the performance in CUPS is shown by:

$$\text{Performance } (CUPS) = \frac{\text{size(Query)} \times \text{size(Database)}}{\text{Total time to complete the computation}} \quad \text{EQN. 4}$$

In some cases, the performance is measured in giga CUPS or GCUPS.

Figure 3:
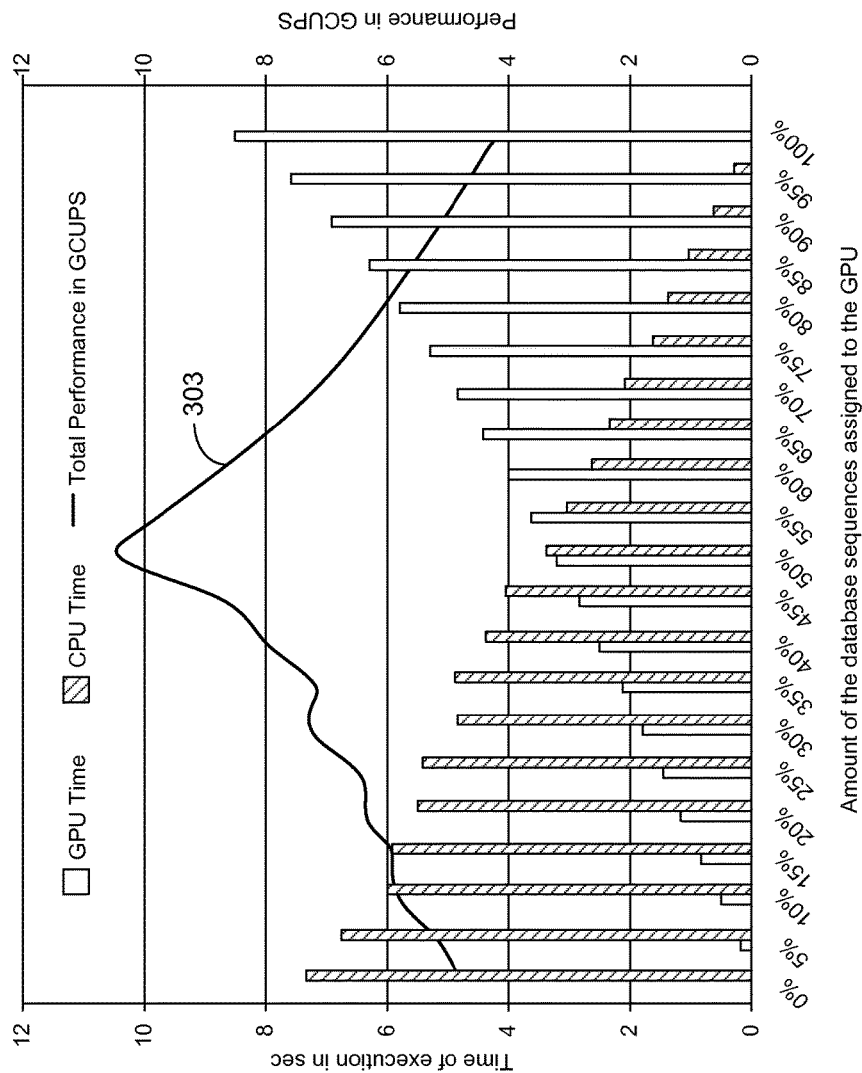
FIG. 3 is a graph illustrating an example of how the performance may change when the portions of the database sequences assigned to a CPU and a GPU are varied in accordance with various embodiments of the present disclosure.

With reference to FIG. 3, shown is an example of how the performance may change (for a query length of 511 amino acid residues) when the portions of the database sequences assigned to the CPU and the GPU are varied. As illustrated in FIG. 3, when all database sequences were assigned to the CPU (i.e., 0% of sequences are assigned to the GPU), an implementation using only the CPU achieved a performance of 4.9 GCUPS, as depicted by curve 303. When the database sequences were distributed between the GPU and the CPU such that the difference between the execution times of the GPU and the CPU was decreased, the total performance 303 in CUPS increased. When the database sequences were distributed such that the execution time of the GPU was almost equal to the execution time of the CPU (between 50% and 55% when the query length is 511 amino acid residues), the highest total performance in GCUPS was achieved. The total performance 303 deteriorates when the difference between the execution times is increased by assigning more database sequences to the GPU. When 100% of the database sequences were assigned to the GPU, the performance was significantly lower than when the databases are split between the CPU and the GPU.

To distribute the database sequences between the GPU and the CPU, "fixed splitting" or "optimized splitting" of the database may be used. In fixed splitting, the database sequences are split between the GPU and the CPU equally. In optimized splitting, the number of database sequences assigned to the GPU and the CPU may be based on the speed of implementation for each processor such that both of them will work in parallel and finish their tasks at the same time.

Figure 4:
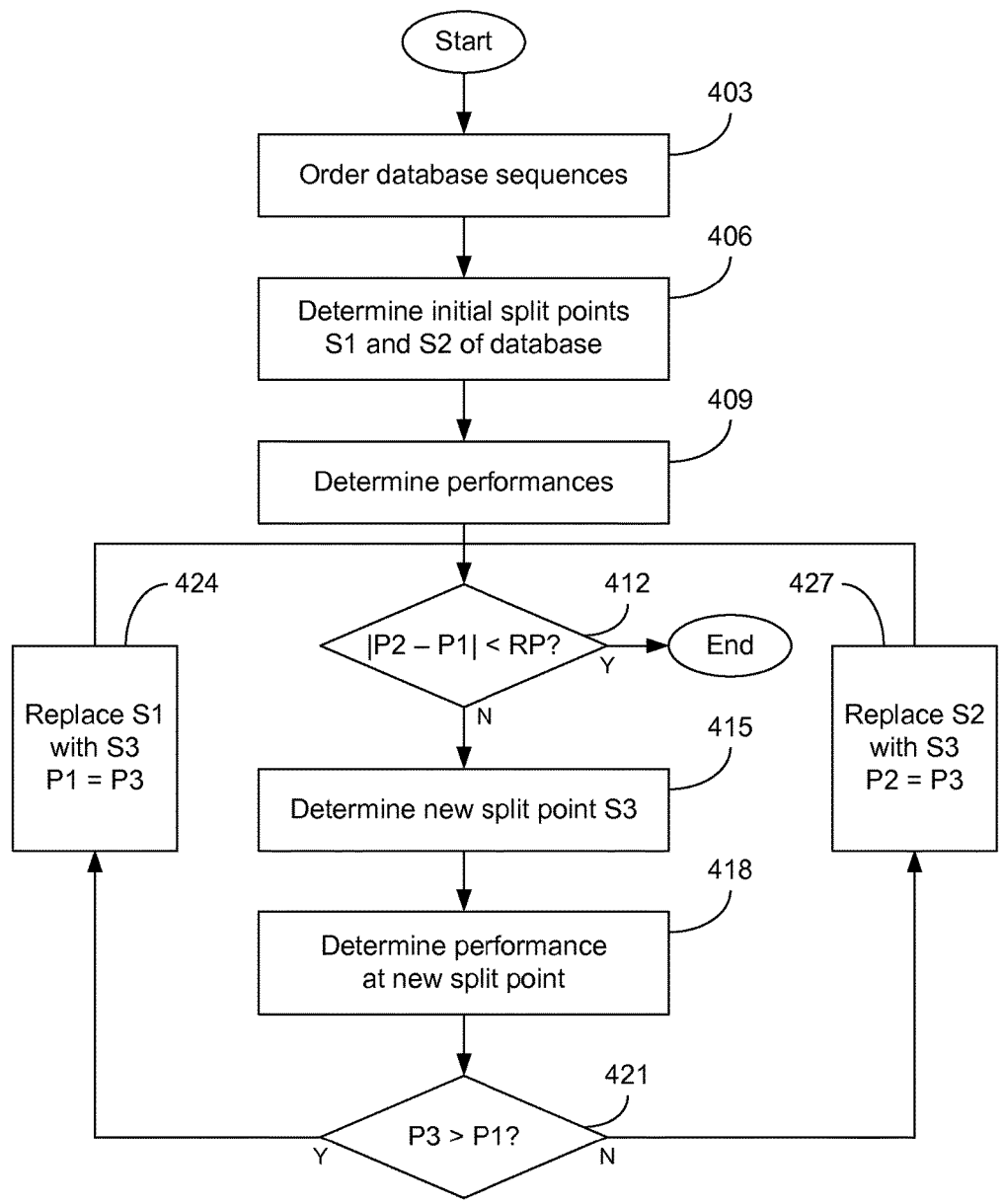
FIG. 4 is a flowchart illustrating an example of optimized splitting for the determination of sequence alignments in accordance with various embodiments of the present disclosure.

Referring next to FIG. 4, shown is a flowchart illustrating an example of optimized splitting, where the performance of the GPU is optimized. Beginning with block 403, the database sequences are sorted according to their length from the longest to the shortest sequences. The sorting may be performed off-line and stored in memory for later access. After sorting the database sequences, two initial split points (S1 and S2) of the sorted database sequences are determined in block 406. For example, the initial split points may be 0% and 100% of the database sequences. For faster splitting of the database sequences, the initial splitting points may be based at least in part upon the performance ratios of the GPU and the CPU.

In block 409, the performance at split point S1 (i.e., P1) and split point S2 (i.e., P2) are determined (e.g., in GCUPS). In block 412, the determined performances are compared (P2−P1). If the difference in performance is less than a predefined performance threshold (e.g., a required precision RP), then split point S1 (or S2) may be considered the splitting ratio associated with the set of database sequences and used for subsequent sequence alignment determinations using that database. In other embodiments, the center or other point between S1 and S2 may be considered the splitting ratio. In some embodiments, the splitting ratio may be associated with a database sequence length such that database sequences longer than that length are assigned to the GPU and the other database sequences are assigned to the CPU.

If the difference in performance is not less than the predefined performance threshold (RP), then a new split point S3 is determined in block 415. For example, the new split point may be based at least in part upon the previous distribution (e.g., the center point between S1 and S2) or may be based upon the determined performances P1 and P2. The performance at the new split point (i.e., P3) is determined (e.g., in GCUPS) in block 418 and compared to the previous performance P1 in block 421. If the performance P3 at the new split point S3 is better than the previous performance P1, then the new split point S3 is assigned to S1 and P1 is equal to P3 in block 424. If not, then S3 is assigned to S2 and P2 is equal to P3 in block 427. The performances P1 and P2 are again compared in block 412. The evaluation continues until the difference in performance is less than the predefined performance threshold (RP) as discussed above. The splitting ratio may be stored in memory for later access. In some embodiments, the database of database sequences may be stored as separate groups of longer database sequences and shorter sequences based upon the splitting ratio.

Below is pseudo code illustrating an example of an application implementing the split determination algorithm of FIG. 4:

```
 1:   Split1 ← 0%                    ▷ Initial splitting point 1
 2:   Split2 ← 100                   ▷ Initial splitting point 2
 3:   P1 = CUPS (Split1)             ▷ Performance at Split 1
 4:   P2 = CUPS (Split2)             ▷ Performance at Split 2
 5:   while (Split1 − Split2) < Required Precision do
 6:       Split3 ← (Split2 + Split1) /2
 7:       P3 = CUPS (Split3)
 8:       if CUPS (Split3) > P1 then
 9:           Split1 ← (Split3)
10:           P1 ← P3
11:       else
12:           Split2 ← (Split3)
13:           P2 ← P3
14:       end if
15:   end while
```

The algorithm starts with two splitting points: Split1 at the 0% ratio of the database and Split2 at the 100% ratio (lines 1 and 2, respectively). After the splitting, the performance in CUPS is computed: P1 for Split1 and P2 for Split2 (lines 3 and 4, respectively). If the difference between the two splits does not meet the required precision, then a new split point Split3 is determined at the middle of the previous two splits (line 6). The performance P3 in CUPS is computed at the new split point (line 7). If this performance P3 is better than the performance at Split1 P1), then split point Split1 will be at the new point Split3 (line 9). Otherwise, split point Split2 will have the new point at Split3 (line 12). The performance in CUPS is computed each time until the difference between the two split points (Split1 and Split2) reaches the required precision.

Figure 5:
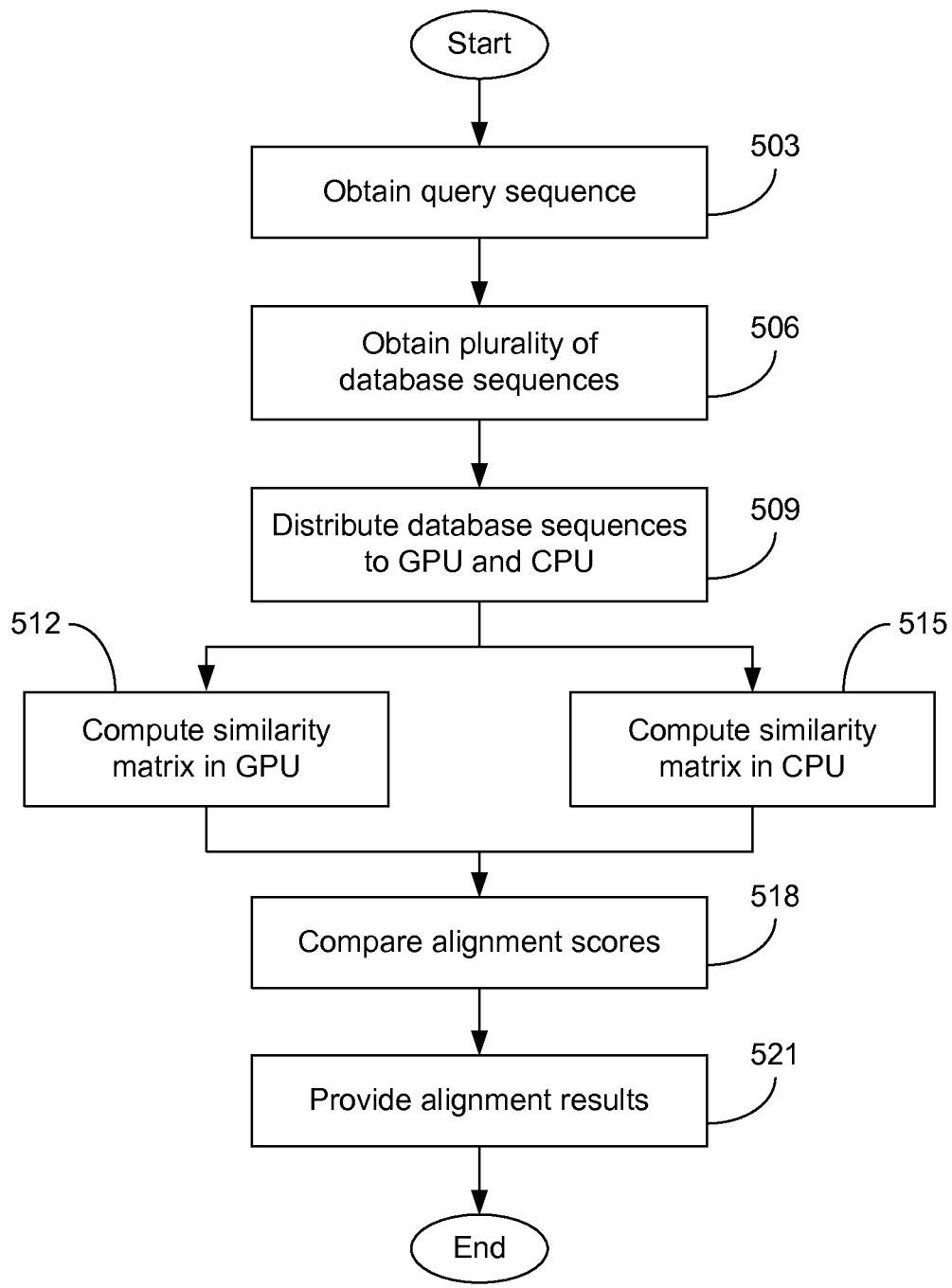
FIG. 5 is a flowchart illustrating an example of a hybrid GPU/CPU evaluation of a query sequence based upon the splitting ratio of FIG. 4 in accordance with various embodiments of the present disclosure.

The splitting ratio may be used later with any new query for aligning a query sequence with the associated database of database sequences. FIG. 5 illustrates the hybrid GPU/CPU evaluation of a query sequence based upon the splitting ratio. Beginning with block 503, a query sequence is obtained. For example, the query sequence may be submitted in a request to perform a sequence alignment evaluation with the set of database sequences. In other implementations, a query sequence may be stored in memory and designated in the request. In block 506, the plurality of database sequences are obtained and distributed in block 509 between a GPU and a CPU based upon the splitting ratio.

The longer database sequences are distributed to the GPU and the shorter database sequences are distributed to the CPU.

In blocks 512 and 515, the GPU and the CPU simultaneously compute the similarity matrices for their respective database sequences and determine the highest alignment scores separately. The maximum alignment score is the final result for aligning the query sequence with the database sequences. The alignment scores from the GPU and the CPU are compared in block 518 to determine the alignment of the query sequence with the whole set of database sequences based upon the maximum alignment score. In some embodiments, the alignment scores from the GPU and a plurality of CPUs are compared in block 518 to determine the alignment of the query sequence with the whole set of database sequences based upon the maximum alignment score. The results of the sequence alignment may then be provided for rendering in block 521.

Figure 6:
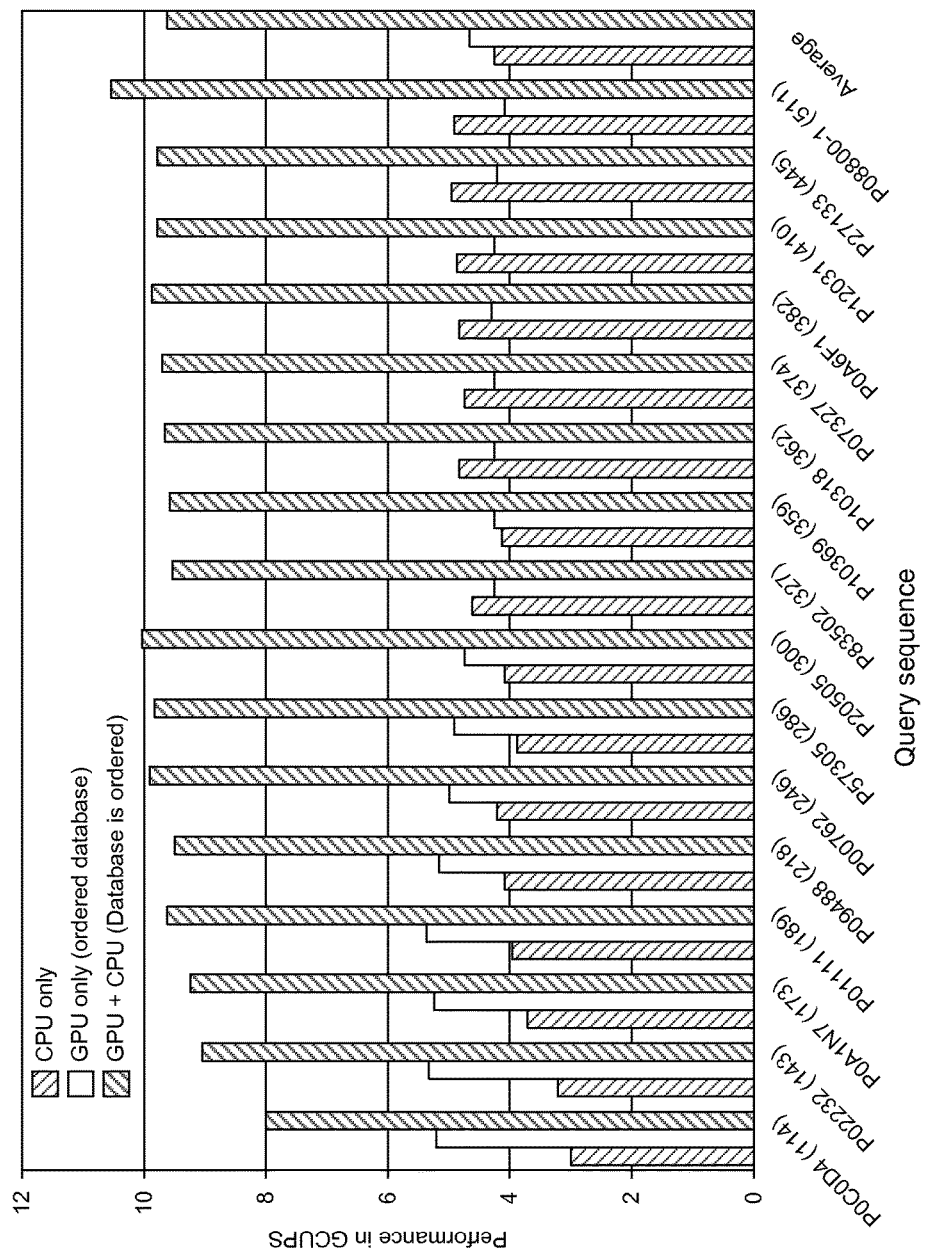
FIGS. 6 and 7 are graphs illustrating the improvement in performance using the hybrid GPU/CPU evaluation of FIG. 5 in accordance with various embodiments of the present disclosure.

Referring to FIG. 6, shown is a bar graph illustrating the effectiveness of performing the hybrid GPU/CPU processing to determine the sequence alignment of the query sequence. The evaluations were conducted using protein sequences from the "SWISS-PROT" database (release 15.12, Dec. 15, 2009). The query sequences were selected to cover a large set of different lengths. The first bar of each query sequence in FIG. 6 shows the performance when only the CPU is used for the sequence alignment. This performance was obtained utilizing Farrar's implementation of the Smith-Waterman (SW) algorithm on an Intel Xeon X5550 CPU with 2.676 GHz. The performance using only the CPU ranged from 3 GCUPS (for a query length of 114 amino acid residues) to 4.9 GCUPS (for a query length of 511 amino acid residues). The average performance for all queries was 4.2 GCUPS.

The second bar of each query sequence in FIG. 6 shows the performance when the SW algorithm is implemented with only an nVidia Quadro FX 4800 GPU with 602 MHz core frequency and 76 GB/Sec memory bandwidth. The performance ranged from 5.2 GCUPS (for a query length of 114 amino acid residues) to 4.1 GCUPS (for a query length of 511 amino acid residues). The average performance for all queries using only the GPU was 4.7 GCUPS.

The third bar of each query sequence in FIG. 6 shows the performance of the SW algorithm implemented with the hybrid GPU/CPU technique of FIG. 5. The third bar shows an improvement in the performance of between 7.9 and 10.5 GCUPS. The average performance for all queries when using the hybrid GPU/CPU technique was 9.6 GCUPS.

Figure 7:
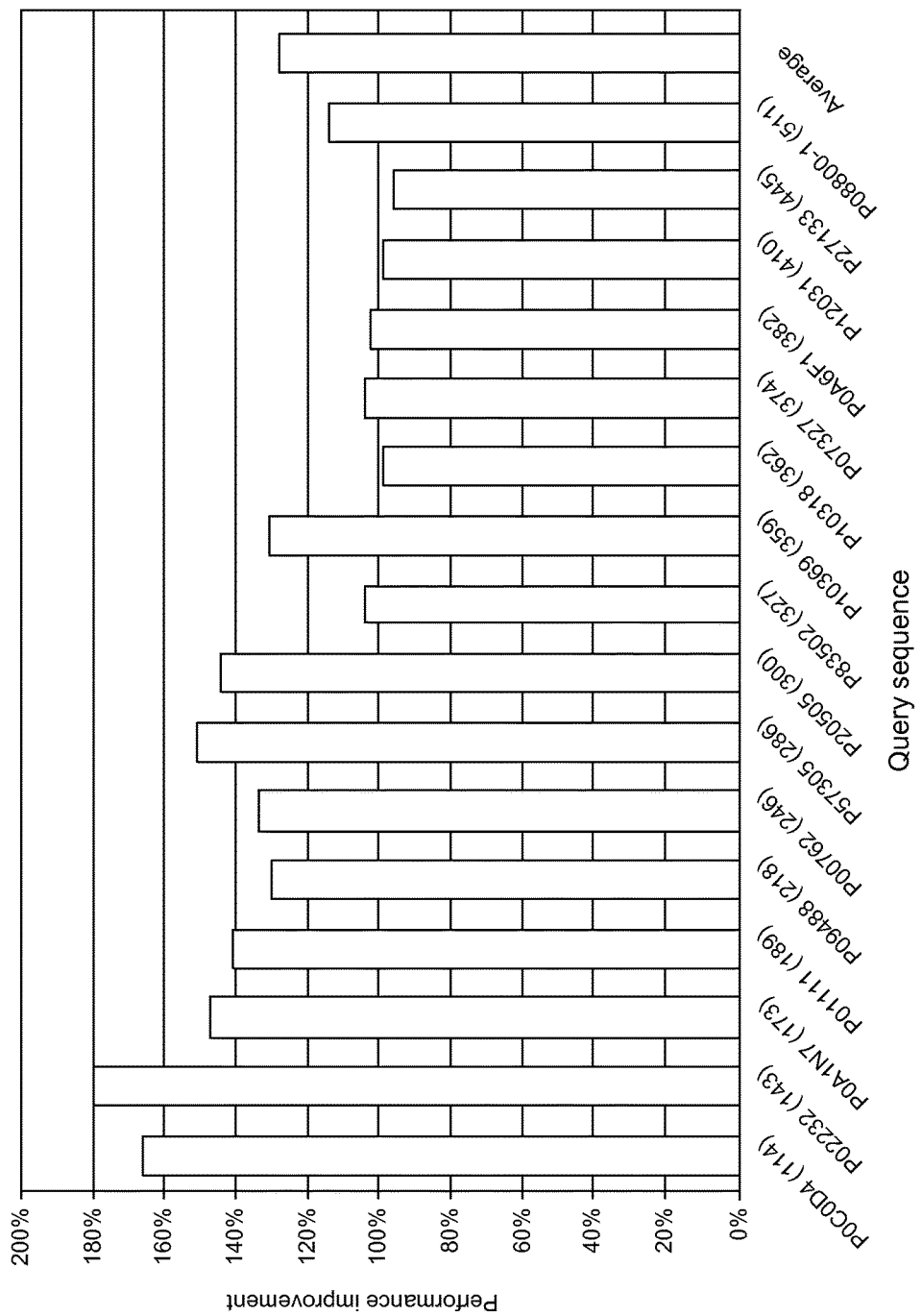

FIG. 7 is a bar graph illustrating the performance improvement of the hybrid GPU/CPU implementation over Farrar's implementation with only a CPU. The average performance of the hybrid GPU/CPU technique exhibited an improvement of a factor of 2.2, and a peak performance improvement by a factor of 2.8 at the query length of 143 amino acid residues.

Figure 8:
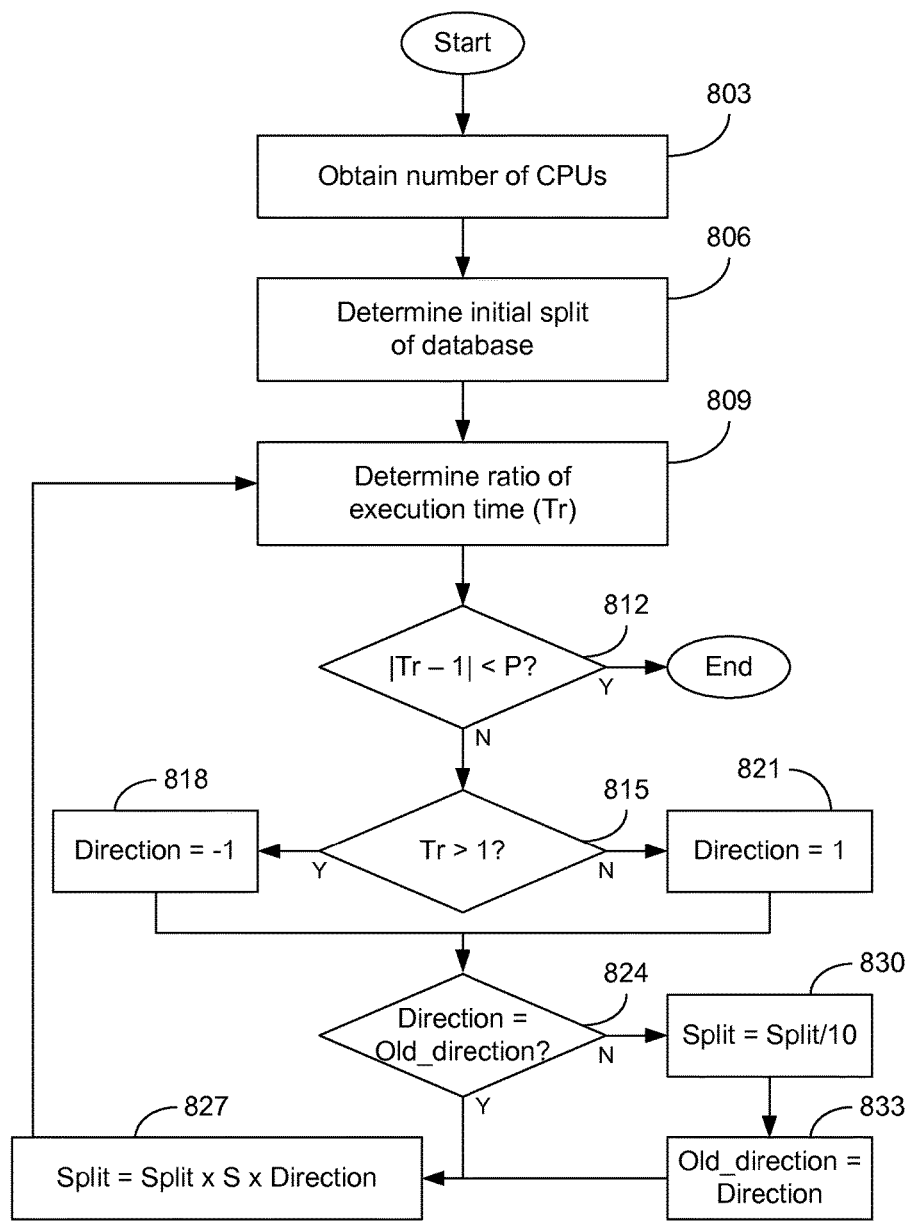
FIG. 8 is a flowchart illustrating another example of optimized splitting for the determination of sequence alignments of FIG. 5 in accordance with various embodiments of the present disclosure.

In some embodiments, a plurality of CPUs may be utilized to compute a similarity matrix for different sets of the shorter database sequences. The additional CPUs can further improve the performance of the sequence alignment. When the system includes a GPU and multiple CPUs, the hybrid GPU/CPU technique may be adapted to work based on the number of the CPUs. With reference to FIG. 8, shown is a flowchart illustrating an example of optimized splitting taking into account the use of a plurality of CPUs. Beginning with block 803, the number of CPUs (N) is obtained. The number of splitting steps (S) and a predefined splitting precision threshold (P) may also be obtained. In block 806, the initial split of the database of database sequences is determined based upon the number of CPUs (N). For example, initially the database sequences may be equally distributed between the GPU and each of the CPUs such that, e.g., the split=100/(N+1) %. The longer sequences are assigned to the GPU.

In block 809, the ratio of the execution time (Tr) between the GPU execution time and the CPU execution time is computed. The GPU and CPU execution times are based upon the database sequence split. For multiple CPUs, the CPU execution time corresponds to the longest CPU execution time of the plurality of CPUs. In block 812, the difference between the GPU and CPU execution times is compared to the splitting precision threshold (P). If the difference in performance is less than P, then the split may be considered the splitting ratio associated with the database of database sequences and used for subsequent sequence alignment determinations using that database. If the difference in performance is not less than splitting precision threshold, then a new split is determined.

In block 815, a splitting direction is determined. If the execution time ratio (Tr) is less than or equal to 1, then the splitting direction is set to negative one in block 818 indicating that the adjustment will be from the beginning of the database towards the end. Otherwise, the splitting direction is set to positive one in block 821 indicating that the adjustment it will be in the reverse direction. If the splitting direction is the same as the old direction of the previous evaluation (block 824), then the database is split between the GPU and the CPU in block 827 based upon the previous split, the splitting steps (S), and the direction.

If in block 824, the splitting direction is not the same as the previous evaluation, then the previous split parameter is reduced (e.g., by a factor of 10) in block 830 and the old direction is updated in block 833. The database is then split between the GPU and the CPU in block 827 based upon the reduced split, the splitting steps (S), and the updated direction. The ratio of the execution time is again determined in block 809 and evaluated in block 812 to determine if the difference in the performance is less than the splitting precision threshold (P). The evaluation continues until the difference in performance is less than P as discussed above. The split may then be considered to be the splitting ratio and may be stored in memory for later access. The splitting ratio may be used later with any new query for aligning a query sequence with the associated with the set of database sequences as discussed with respect to FIG. 6.

When more than one CPU is indicated in the input, the shorter database sequences assigned to the CPUs may be distributed equally between all of the CPUs. In other embodiments, the shorter database sequences may be distributed the CPUs to equalize the execution times of the CPUs.

Figure 10:
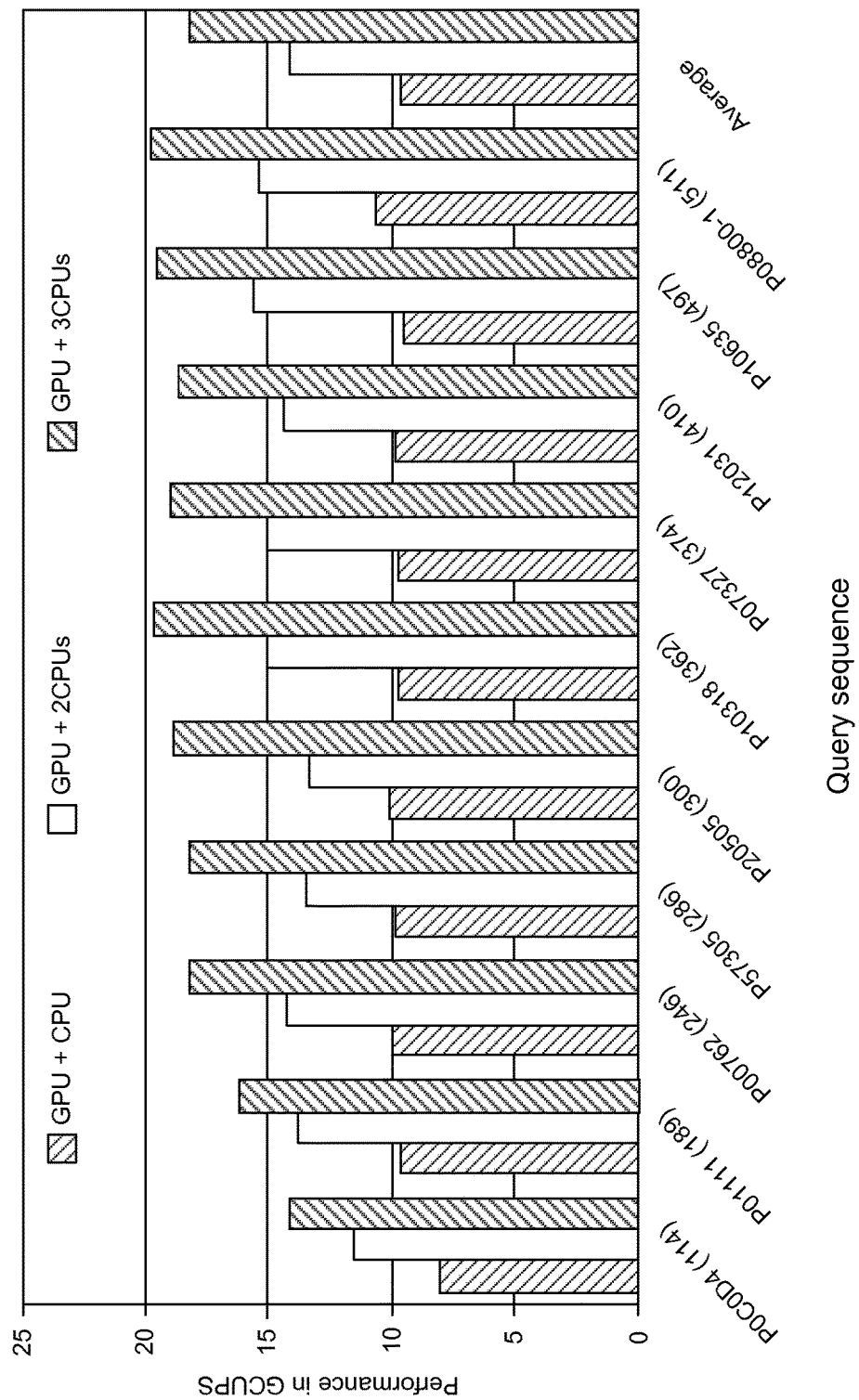

Referring to FIGS. 9 and 10, shown the performance results for three types of hybrid systems: GPU+CPU, GPU+2CPUs, and GPU+3CPUs, for different lengths of queries. The evaluations were conducted using protein sequences from the "SWISS-PROT" database (release 15.12, Dec. 15, 2009). The query sequences were selected to cover a large set of different lengths. The performance was obtained by utilizing an Intel Xeon X5550 CPU with 2.676 GHz and an nVidia Quadro FX 4800 GPU with 602 MHz core frequency and 76 GB/Sec memory bandwidth.

The workload was distributed between the GPU and the CPUs based upon the number of CPUs given as input to the technique and based on the execution time of the processor units. FIG. 9 shows the percentage of the database sequences assigned to the GPU for the three hybrid systems. For example, in the GPU+CPU platform and for the query length of 114 amino acid residues, 65% of the database is assigned to the GPU, while 35% is assigned to the CPU. But in the case of the GPU+3CPUs' platform and for the same query length (i.e., 114), 40% of the database is assigned to the GPU, while 60% is assigned to the 3 CPUs (i.e., 20% of the database is assigned to each CPU). FIG. 10 shows the performance results after distributing the workload between the processor units and is based on the number of CPUs given as input to the technique. The peak performance is improved to 10.6 GCUPS, 15.5 GCUPS, and 19.8 GCUPS for the platforms GPU+CPU, GPU+2CPUs, and GPU+3CPUs, respectively.

Using optimized splitting also exhibits improved performance results in comparison to the performance achieved using fixed splitting. For example, in the case of the GPU+3CPUs platform, each processor works on 25% of the database. With the workload equally distributed between the GPU and the CPUs in each hybrid platform using fixed splitting, the peak performance for the GPU+CPU, GPU+2CPUs, and GPU+3CPUs platforms was 10.4 GCUPS, 13.7 GCUPS, and 18.6 GCUPS, respectively (which is achieved with the query length of 511 amino acid residues).

Figure 11:
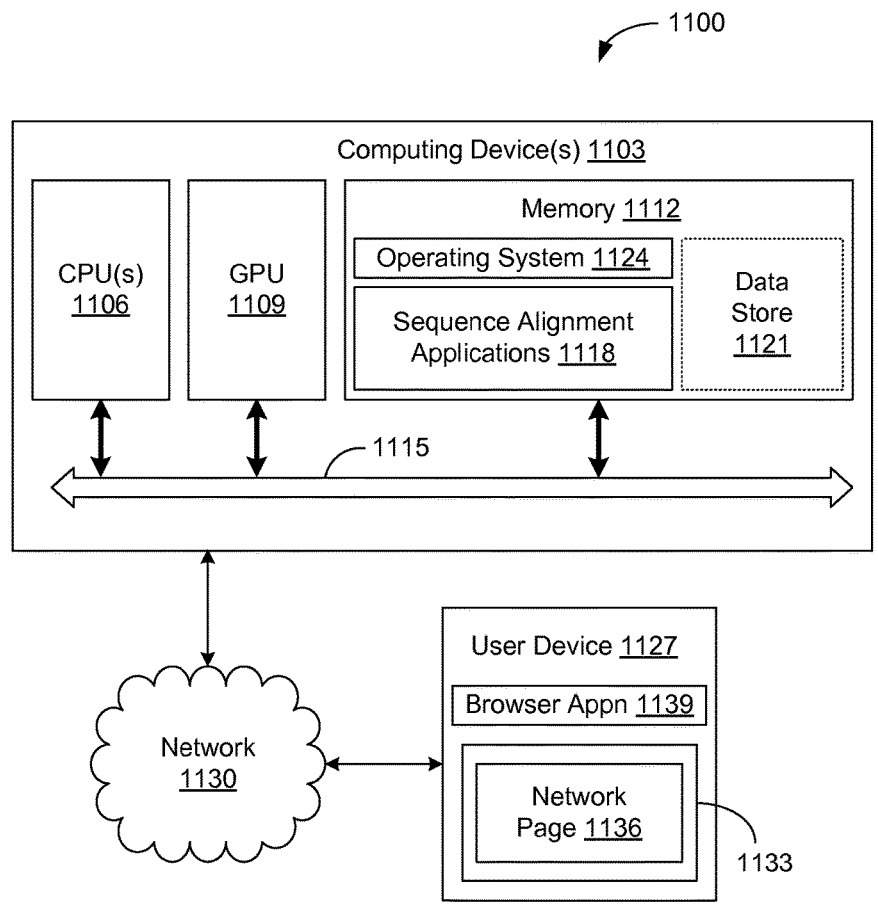
FIG. 11 is a graphical representation of an example of a hybrid GPU/CPU system for executing sequence alignment applications of FIGS. 4, 5, and 8 in accordance with various embodiments of the present disclosure.

Referring now to FIG. 11, shown is an example of a hybrid GPU/CPU system 1100 for evaluating sequence alignments. The system 1100 includes one or more computing device(s) 1103. The computing device 1103 includes at least one processor circuit, for example, having at least one central processing unit (CPU) 1106, a graphics processing unit (GPU) 1109, and a memory 1112, all of which are coupled to a local interface 1115. The CPU(s) 1106 may be, e.g., a CPU such as an Intel Xeon X5550 CPU (2.676 GHz) and the GPU 1109 may be, e.g., an nVidia Quadro FX 4800. To this end, the computing device(s) 1103 may comprise, for example, a server computer or any other system providing computing capability: Alternatively, a plurality of computing devices 1103 may be employed that are arranged, for example, in one or more server banks or computer banks or other arrangements. For example, a plurality of computing devices 1103 together may comprise, for example, a cloud computing resource, a grid computing resource, and/or any other distributed computing arrangement. Such computing devices 1103 may be located in a single installation or may be dispersed among many different geographical locations. For purposes of convenience, the computing device 1103 is referred to herein in the singular. Even though the computing device 1103 is referred to in the singular, it is understood that a plurality of computing devices 1103 may be employed in the various arrangements as described above. The local interface 1115 may comprise, for example, a data bus with an accompanying address/control bus or other bus structure as can be appreciated.

Stored in the memory 1112 are both data and several components that are executable by the CPU(s) 1106 and/or GPU 1109. In particular, stored in the memory 1112 and executable by the CPU(s) 1106 and/or GPU 1109 are sequence alignment applications 1118 and potentially other applications. Also stored in the memory 1112 may be a data store 1121 and other data. The data stored in the data store 1121, for example, is associated with the operation of the various applications and/or functional entities described below. For example, the data store may include sequence databases, splitting ratios associated with the sequence databases, query sequences, and other data or information as can be understood. In addition, an operating system 1124 may be stored in the memory 1112 and executable by the CPU(s) 1106. The data store 1121 may be may be located in a single computing device or may be dispersed among many different devices.

The system may also include one or more user device(s) 1127. The user device 1127 is representative of a plurality of user devices that may be communicatively coupled to the computing device 1103 through a network 1130 such as, e.g., the Internet, intranets, extranets, wide area networks (WANs), local area networks (LANs), wired networks, wireless networks, networks configured for communication over a power grid, or other suitable networks, etc., or any combination of two or more such networks. In some embodiments, a user device 1127 may be directly connected to the computing device 1103.

The user device 1127 may comprise, for example, a processor-based system such as a computer system. Such a computer system may be embodied in the form of a desktop computer, a laptop computer, a personal digital assistant, a cellular telephone, web pads, tablet computer systems, or other devices with like capability. The user device 1127 includes a display device 1133 upon which various network pages 1136 and other content may be rendered. The user device 1127 may be configured to execute various applications such as a browser application 1139 and/or other applications. The browser application 1139 may be executed in a user device 1127, for example, to access and render network pages 1136, such as web pages, or other network content served up by the computing device 1103 and/or other servers. The user device 1127 may be configured to execute applications beyond browser application 1139 such as, for example, e-mail applications, instant message (IM) applications, and/or other applications.

The components executed on the computing device 1103 include, for example, sequence alignment applications 1118 and other systems, applications, services, processes, engines, or functionality not discussed in detail herein. The sequence alignment applications 1118 are executed in order to facilitate the evaluation of alignment of a query sequence with database sequences included in a database. The sequence alignment applications 1118 may generate network pages 1136 such as web pages or other types of network content that are provided to a user device 1127 in response to a request for the purpose of evaluating a sequence alignment. While sequence alignment has been discussed with respect to bioinformatics such as DNA or protein sequence matching, it may be applied to other research areas for different purposes such as video, audio, or image copy detection, text plagiarism detection, etc.

It is understood that there may be other applications that are stored in the memory 1112 and are executable by the CPU(s) 1106 and/or GPU 1109 as can be appreciated. Where any component discussed herein is implemented in the form of software, any one of a number of programming languages may be employed such as, for example, C, C++, C#, Objective C, Java, Java Script, Perl, PHP, Visual Basic, Python, Ruby, Delphi, Flash, or other programming languages.

A number of software components are stored in the memory 1112 and are executable by the CPU(s) 1106 and/or GPU 1109. In this respect, the term "executable" means a program file that is in a form that can ultimately be run by the CPU(s) 1106 and/or GPU 1109. Examples of executable programs may be, for example, a compiled program that can be translated into machine code in a format that can be loaded into a random access portion of the memory 1112 and run by the CPU(s) 1106 and/or GPU 1109, source code that may be expressed in proper format such as object code that is capable of being loaded into a random access portion of the memory 1112 and executed by the CPU(s) 1106 and/or GPU 1109, or source code that may be interpreted by another executable program to generate instructions in a random access portion of the memory 1112 to be executed by the CPU(s) 1106, GPU 1109, etc. An executable program may be stored in any portion or component of the memory 1112 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1112 is defined herein as including both volatile and nonvolatile memory and data storage components. Volatile components are those that do not retain data values upon loss of power. Nonvolatile components are those that retain data upon a loss of power. Thus, the memory 1112 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the CPU 1106 may represent multiple CPUs 1106, the GPU 1109 may represent multiple GPUs 1109, and the memory 1112 may represent multiple memories 1112 that operate in parallel processing circuits, respectively. In such a case, the local interface 1115 may be an appropriate network that facilitates communication between any two of the multiple CPU(s) 1106 and/or GPU 1109, between any CPU(s) 1106 and/or GPU 1109 and any of the memories 1112, or between any two of the memories 1112, etc. The local interface 1115 may comprise additional systems designed to coordinate this communication, including, for example, performing load balancing. The CPU(s) 1106 and/or GPU 1109 may be of electrical or of some other available construction.

Although the sequence alignment applications 1118, and other various systems described herein, may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

The flowcharts of FIGS. 4, 5, and 8 show the functionality and operation of an implementation of portions of the sequence alignment applications 1118. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a CPU(s) 1106 and/or GPU 1109 in a computer system or other system. The machine code may be converted from the source code, etc. If embodied in hardware, each block may represent a circuit or a number of interconnected circuits to implement the specified logical function(s).

Although the flowcharts of FIGS. 4, 5, and 8 show a specific order of execution, it is understood that the order of execution may differ from that which is depicted. For example, the order of execution of two or more blocks may be scrambled relative to the order shown. Also, two or more blocks shown in succession in FIGS. 4, 5, and 8 may be executed concurrently or with partial concurrence. Further, in some embodiments, one or more of the blocks shown in FIGS. 4, 5, and 8 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including sequence alignment applications 1118, that comprise software or code can be embodied in any non-transitory computer-readable medium for use by or in connection with an instruction execution system such as, for example, a CPU(s) 1106 and/or GPU 1109 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, electronic, magnetic, optical, electromagnetic, infrared, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, at least the following is claimed:
1. A system, comprising:
   at least one computing device; and
   an application executed in the at least one computing device, the application comprising:
      logic that obtains a plurality of database sequences;
      logic that orders the plurality of database sequences;
      logic that determines a splitting ratio associated with the ordered plurality of database sequences, where the splitting ratio separates the ordered plurality of database sequences into a first portion of the ordered plurality of database sequences associated with at least one central processing unit (CPU) and a second portion of the ordered plurality of database sequences associated with a graphical processing unit (GPU), where the length of the database sequences of the first portion of the ordered plurality of database sequences are shorter than the length of the database sequences of the second portion of the ordered plurality of database sequences;
      logic that assigns the first portion of the ordered plurality of database sequences to the at least one CPU for sequencing by the at least one CPU; and
      logic that assigns the second portion of database sequences to the GPU for sequencing by the GPU.

2. The system of claim 1, wherein the splitting ratio is determined based at least in part upon a difference between an execution time of the CPU for sequencing individual ones of the ordered plurality of database sequences and an execution time of the GPU for sequencing individual ones of the ordered plurality of database sequences.

3. The system of claim 2, wherein the splitting ratio is determined when the difference between the execution time of the CPU and the execution time of the GPU is within a predefined threshold.

4. The system of claim 1, wherein the logic that determines the splitting ratio further comprises:
   logic that splits the ordered plurality of database sequences;
   logic that determines an execution time of the CPU for each portion of the split ordered plurality of database sequences and the execution time of the GPU for each portion of the split ordered plurality of database sequences; and
   logic that determines if a difference between the execution time of the CPU and the execution time of the GPU is within a predefined threshold.

5. The system of claim 4, wherein the logic that determines the splitting ratio further comprises logic that determines a new split of the ordered plurality of database sequences when the difference between the execution time of the CPU and the execution time of the GPU is not within the predefined threshold.

6. The system of claim 1, wherein the logic that determines the splitting ratio further comprises:
   logic that determines a first split point and a second split point of the ordered plurality of database sequences; and
   logic that determines the splitting ratio based upon performance of the GPU corresponding to the first split point and the performance of the GPU corresponding to the second split point.

7. The system of claim 6, wherein the splitting ratio is determined when the difference between the performance of the GPU corresponding to the first split point and the performance of the GPU corresponding to the second split point is within a predefined threshold.

8. The system of claim 6, wherein the logic that determines the splitting ratio further comprises logic that determines a new split point when the difference between the performance of the GPU corresponding to the first split point and the performance of the GPU corresponding to the second split point is not within a predefined threshold.

9. A computer-implemented method, comprising:
   obtaining, via a computing device, a plurality of database sequences;
   ordering, via the computing device, the plurality of database sequences; and
   determining, via the computing device, a splitting ratio associated with the ordered plurality of database sequences, where the splitting ratio separates the ordered plurality of database sequences into a first portion of the ordered plurality of database sequences associated with at least one central processing unit (CPU) and a second portion of the ordered plurality of database sequences associated with a graphical processing unit (GPU), where the length of the database sequences of the first portion of the ordered plurality of database sequences are shorter than the length of the database sequences of the second portion of the ordered plurality of database sequences;
   assigning, via the computing device, the first portion of the ordered plurality of database sequences to the at least one CPU for sequencing by the at least one CPU; and
   assigning, via the computing device, the second portion of database sequences to the GPU for sequencing by the GPU.

10. The computer-implemented method of claim 9, wherein the splitting ratio is determined based at least in part upon a difference between an execution time of the CPU for sequencing individual ones of the ordered plurality of database sequences and an execution time of the GPU for sequencing individual ones of the ordered plurality of database sequences.

11. The computer-implemented method of claim 10, wherein the splitting ratio is determined when the difference between the execution time of the CPU and the execution time of the GPU is within a predefined threshold.

12. The computer-implemented method of claim 10, wherein determining, via the computing device, the splitting ratio comprises:
   splitting, via the computing device, the ordered plurality of database sequences;
   determining, via the computing device, the execution time of the CPU for each portion of the split ordered plurality of database sequences and the execution time of the GPU for each portion of the split ordered plurality of database sequences; and
   determining, via the computing device, if the difference between the execution time of the CPU and the execution time of the GPU is within a predefined threshold.

13. The computer-implemented method of claim 12, wherein determining, via the computing device, the splitting ratio further comprises determining, via the computing device, a new split of the ordered plurality of database sequences when the difference between the execution time of the CPU and the execution time of the GPU is not within the predefined threshold.

14. The computer-implemented method of claim 9, wherein determining, via the computing device, the splitting ratio further comprises:

determining, via the computing device, a first split point and a second split point of the ordered plurality of database sequences; and determining, via the computing device, the splitting ratio based upon performance of the GPU corresponding to the first split point and the performance of the GPU corresponding to the second split point.

15. The computer-implemented method of claim 14, wherein the splitting ratio is determined when a difference between the performance of the GPU corresponding to the first split point and the performance of the GPU corresponding to the second split point is within a predefined threshold.

16. The computer-implemented method of claim 14, wherein determining, via the computing device, the splitting ratio further comprises determining, via the computing device, a new split point when the difference between the performance of the GPU corresponding to the first split point and the performance of the GPU corresponding to the second split point is not within a predefined threshold.

* * * * *